United States Patent [19]

Richards et al.

[11] Patent Number: 4,994,082

[45] Date of Patent: Feb. 19, 1991

[54] ACCOMMODATING INTRAOCULAR LENS

[75] Inventors: William D. Richards, Medway; Ernesto E. Blanco, Belmont, both of Mass.

[73] Assignee: Ophthalmic Ventures Limited Partnership, Norwood, Mass.

[21] Appl. No.: 242,962

[22] Filed: Sep. 9, 1988

[51] Int. Cl.$^5$ .............................................. A61F 2/16
[52] U.S. Cl. ......................................................... 623/6
[58] Field of Search ............................................ 623/6

[56] References Cited

U.S. PATENT DOCUMENTS 4,253,199  3/1981  Banko ..................................... 623/6
4,409,691  10/1983  Levy ...................................... 623/6

FOREIGN PATENT DOCUMENTS 0166051  1/1986  European Pat. Off. ............... 623/6

Primary Examiner—Ronald Frinks
Attorney, Agent, or Firm—Schiller, Pandiscio & Kusmer

[57] ABSTRACT

An intraocular lens assembly including an adjustable-power lens assembly and an adjustment mechanism coupled between the lens assembly and the ciliary muscle of the eye in which the lens assembly is implanted for adjusting the power of the lens assembly in response to contraction or relaxation of the ciliary muscle.

17 Claims, 2 Drawing Sheets

ACCOMMODATING INTRAOCULAR LENS

BACKGROUND OF THE INVENTION

The present invention relates generally to surgical implant devices and more particularly to intraocular lenses.

As persons age, their eyes typically loose the ability to change focus quickly and to clearly focus on close, distant and intermediately-positioned objects. Because of this loss of accommodation in the human eye, persons reaching their early forties often find it necessary to wear reading glasses to clearly focus on closely-positioned objects.

An even more pronounced loss of accommodation typically occurs when the crystalline lens is replaced by a conventional intraocular lens. Such replacement is performed, as is well known, in response to the formation of cataracts in the crystalline lens or when the crystalline lens is damaged by disease or injury. It has been recognized that with time the ciliary muscle of the eye develops the ability to move the intraocular lens back and forth along its center axis, thereby changing the focal point of the light rays passing through the intraocular lens and reaching the retina. Less than one diopter of power change is believed to occur pursuant to this movement. This minimal accommodation is insufficient to permit an individual to focus on close and distant objects, since 3 to 6 diopters of power change is typically required to achieve this range of change in focus.

In an attempt to overcome loss of accommodation in the eye, bifocal intraocular lenses have been developed. These lenses include a relatively thick center section comprising a minor portion of the entire diameter of the lens and a relatively thin peripheral section surrounding the center portion and having a thickness substantially equal to that of conventional intraocular lenses. The thicker center section has a focal power that is selected to permit the eye to focus on close objects and the thin peripheral section has a focal power that is selected to permit the eye to focus on distant objects.

When an eye containing such a bifocal intraocular lens is focused on a close object, the iris of the eye closes down. As a result, only the light rays passing through the thick center section of the lens reach the retina, whereby the closely-positioned object appears in focus. On the other hand, when the eye is focused on distant objects, the majority of light rays passing through the bifocal intraocular lens pass through the peripheral section thereof (because the peripheral section comprises the majority of the bifocal intraocular lens), whereby the distant objects appear in focus. Because only a small percentage of the light rays traveling through the bifocal lens in an eye focused on a distant object pass through the thick center section, the mind is able to ignore these rays with the result that these differently-focused light rays are not visible.

Although the bifocal intraocular lens has improved accommodation capabilities as compared to a conventional intraocular lens, the former does not provide the type and degree of accommodation provided by the crystalline lens of a young person's eye. Specifically, the bifocal intraocular lens refracts incoming light rays such that viewed objects are in focus at substantially only two focal lengths, typically close and distant. By way of contrast, a young person's eye varies the focus in analog fashion between close and distant objects so that objects at all focal lengths (assuming the person has 20/20 vision) are in focus. Hence, it is a significant drawback of the bifocal intraocular lens that it cannot provide the continuum of focal powers required to permit clear focusing on close, distant and intermediately-positioned objects.

SUMMARY OF THE INVENTION

An object of the present invention is to provide an intraocular lens which will provide the human eye in which is it implanted with an accommodation capability substantially equal to that of a typical young person's eye.

Another object of the present invention is to provide an intraocular lens which will permit the human eye in which it is implanted to change focus automatically in analog fashion so as to permit the eye to clearly focus on objects positioned at close, intermediate and distant locations.

Yet another object of the present invention is to provide an accommodating intraocular lens which is easily implantable, readily accepted by the human eye and will function satisfactorily for an extended period of time.

These and other objects are achieved by an adjustable-power intraocular lens comprising a lens assembly and an adjustment mechanism or haptics coupled between the lens assembly and the ciliary muscle of the eye. In a first embodiment of the present invention the lens assembly comprises a single progressive power lens. In this embodiment, the haptics are adapted to move the lens normally to the center axis thereof so as to progressively change the focal power of the lens. In a second embodiment of the present invention the lens assembly comprises a pair of compound lens positioned so that their center axes are coaxial. In this second embodiment the haptics are adapted to move the lenses toward and away from one another along the center axes thereof so as to change the focal power of the lens assembly. In a third embodiment of the present invention, a pair of progressive lenses are positioned so that their center axes are coaxial or extend in parallel, with the higher power side of one of the progressive lenses being diametrically opposed to the higher power side of the other. In this third embodiment, the haptics are adapted to move both of the lenses normally to their center axes so as to progressively change the focal power of the lens assembly.

BRIEF DESCRIPTION OF THE DRAWINGS

Other objects, features and advantages of the invention are set forth in the following specific description of a preferred embodiment of the invention and the accompanying drawings wherein.

In the drawings, like reference numerals refer to like parts.

DETAILED DESCRIPTION OF THE INVENTION

Referring to FIGS. 1-6, the present invention is an accommodating intraocular lens comprising a lens assembly 20 and an adjustment mechanism, or haptics, 30 coupled between the lens assembly and the sulcus of the ciliary muscle 40 of the eye in which the accommodating intraocular lens 20 is implanted. Haptics 30 transmit muscle motion from ciliary muscle 40 to lens assembly 20 so as to change the focal power of the latter, as described more fully hereinafter.

As is known, the ciliary muscle 40 surrounds the crystalline lens and has a roughly annular shape. As the ciliary muscle contracts and relaxes about its central axis, the diameter of the center aperture thereof decreases and increases, respectively. This contracting and expanding motion is transmitted to the crystalline lens by zonular fibers which extend between the lens equator and the sulcus of the ciliary muscle. When the ciliary muscle relaxes, the center aperture thereof enlarges pulling the zonular fibers away from the lens. The zonular fibers in turn stretch the lens radially thereby decreasing the thickness and curvature thereof, and hence, decreasing the focal power of the lens. Alternatively, when the ciliary muscle contracts, the center opening thereof closes up allowing the zonular fibers to relax. This relaxation in turn removes the radial stretching force applied to the lens thereby permitting the lens to regain its normal thicker, more curved configuration. The lens has a higher focal power when in this thicker more curved configuration.

Figure 1:
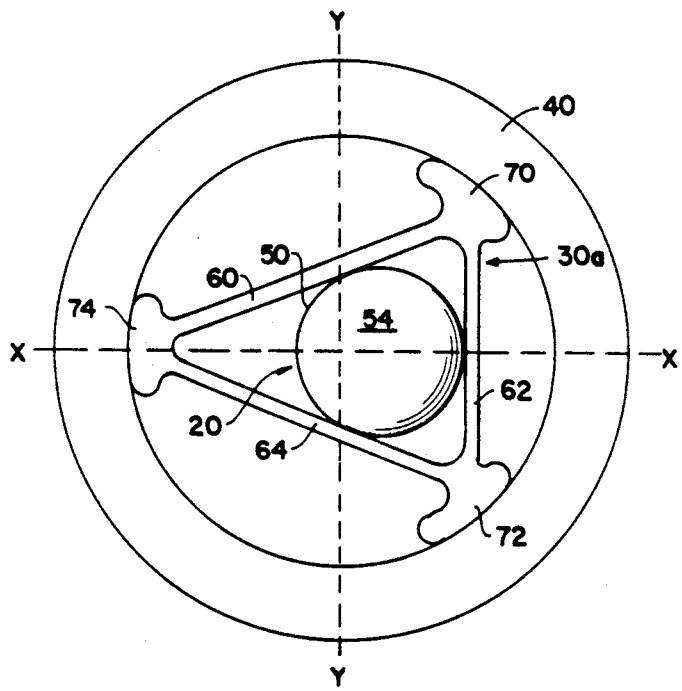
FIG. 1 is a front elevation view of the first embodiment of the present invention, including a schematic representation of the ciliary muscle in which the first embodiment is disposed.
Figure 2:
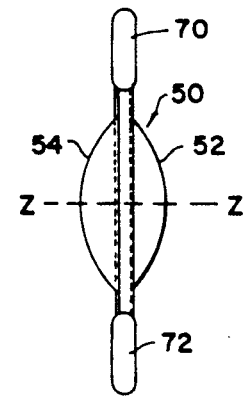
FIG. 2 is a side elevation view of the embodiment illustrated in FIG. 1.

Referring to FIGS. 1 and 2, the lens assembly 20 of the first embodiment of the present invention comprises a single progressive power convex lens 50 sized to fit within the capsule which encased the crystalline lens or, alternatively, sized to fit within the sulcus of the ciliary muscle slightly in front of the capsule which encased the crystalline lens. Lens 50 is preferably circular and preferably comprises a convex base power surface 52 and a progressive power surface 54. Alternatively, base power surface 52 may also have a progressive power configuration, may be planar or may take the configuration of a fresnel lens.

Progressive power outer surface 54 is also convex. In accordance with the conventional design of progressive power lenses, the radius of curvature of surface 54, as viewed in FIG. 1, measured along lines extending coincident or in parallel with the Y axis decreases substantially linearly from left to right along the X axis. This curvature is selected so that the focal point or plane of light rays passing through lens 50 and progressive outer surface 54 will vary depending upon where along the X axis of the latter the light rays pass. Light rays passing through the portions of progressive power surface 54 having the smallest radius of curvature will converge at a focal point or plane that is closer to surface 54 than the focal point or plane at which those rays passing through portions of surface 54 having a greater radius of curvature will converge.

The adjustment mechanism, or haptics, 30a of the first embodiment of the present invention is designed to transmit contraction and relaxation of the ciliary muscle to lens 50 so as to cause the latter to move back and forth along the X axis, as viewed in FIG. 1, substantially normally to the center or Z axis thereof, as seen in FIG. 2. The center or Z axis extends through the diametrical center of base power surface 52 and progressive power surface 54 and extends normally to these surfaces at the diametrical centers thereof.

In the most general sense, haptics 30a comprise two or more support members, each of which mechanically couple lens 50 to the ciliary muscle and are constructed to transmit the contraction and relaxation motion of the ciliary muscle to the lens so as to cause the lens to move back and forth along the X axis, as viewed in FIG. 1. The support members engage different portions of the lens and are formed so as to have specifically defined points of flexure. By selective positioning of the support members on the lens and by proper definition of the points of flexure of the support members, haptics 30a will cause lens 20 to move in a first direction along the X axis when the ciliary muscle contracts and in an opposite direction along the X axis when the ciliary muscle relaxes.

Referring to FIGS. 1 and 2, the haptics 30a of the first embodiment of the present invention may, for instance, comprise elongate arms 60, 62 and 64. Preferably, these arms are made from a plastic having suitable biological compatibility and selected flexure and strength characteristics. A central portion of each of these arms engages, is secured to, or is integral with the outer edge of lens 50, with the arms being positioned so that the central portion of each arm is separated by about 120° from the central portions of adjacent arms, as measured around the circumference of lens 50. More specifically, arms 60 and 64 slidingly engage the outer edge of lens 50 and the center of arm 62 is attached to or is integral with the high power side of lens 50 at about the 3 o'clock position, as seen in FIG. 1. Alternatively, as described in greater detail below, the low power side of lens 50 may be attached to the center of arm 62. Optionally, an upstanding flange (not shown) may be provided running along the length of the inner edges of arms 60 and 64 and a groove may be provided in the circumferential edge of lens 50 for receiving the flanges with a sliding fit. Alternatively, a groove (not shown) may be provided running along the length of the inner edges of arms 60 and 64 and an upstanding flange (not shown) may be provided along the circumferential edge of lens 50 for being received in the grooves with a sliding fit.

Arms 60 and 64 are more resistant to flex along their length than arm 62. In addition, arm 62 is preferably biased to flex inwardly to the left along its length, as viewed in FIG. 1, when a compressive force is applied to the ends of arm 62. Alternatively, arm 62 may be biased to flex outwardly to the right, as viewed in FIG. 1. These flexural characteristics are achieved, as one of ordinary skill in the art will readily appreciate, by selective design of the arms and by proper choice of material used to fabricate the arms. As described in greater detail hereinafter, these flexural characteristics-are selected so that when the ciliary muscle contracts and relaxes, arms 60, 62 and 64 will flex so as to cause lens 50 to move back and forth along the X axis, as viewed in FIG. 1, normally to the center or Z axis, as viewed in FIG. 2.

The haptics 30a of the first embodiment further comprise curved end portions 70, 72 and 74. The thickness and radius of curvature of the latter as well as the length of arms 60, 62, and 64, are selected to permit the end portions to fit securely within the sulcus of the ciliary muscle 40, even when the latter is fully relaxed.

The ends of arms 60 and 62 are secured together at or are integral with end portion 70, the ends of arms 62 and 64 are secured together at or are integral with end portion 72, and the ends of arms 60 and 64 are secured together at or are integral with end portion 74. The lengths of arms 60, 62 and 64 are selected so that each of the end portions 70, 72 and 74 is separated by about 120° from adjacent end portions, whereby the arms 60, 62 and 64 define a triangularly-shaped structure which fits securely within the sulcus of the ciliary muscle. Preferably, arms 60 and 64 are secured to end portions 70, 72 and 74 so as to lie along a first plane and arm 62 is secured to end portions 70 and 72 so as to lie along a second plane that is spaced from but extends in parallel with the first plane. Arms 60, 62 and 64 are positioned relative to lens 50 so that arm 62 extends substantially parallel to the Y axis, as viewed in FIG. 1.

The haptics 30a of the first embodiment illustrated in FIGS. 1 and 2 are only exemplary of the structure the haptics may take. It should be appreciated that the haptics of the first embodiment may comprise a wide range of structure, the only requirements being that the haptics (a) securely support the progressive power lens 50 within the eye and (b) translate the contraction and relaxation motion of the ciliary muscle into a force which moves lens 50 back and forth along the X axis, as seen in FIG. 1, normally to the center or Z as seen in FIG. 2.

Figure 3:
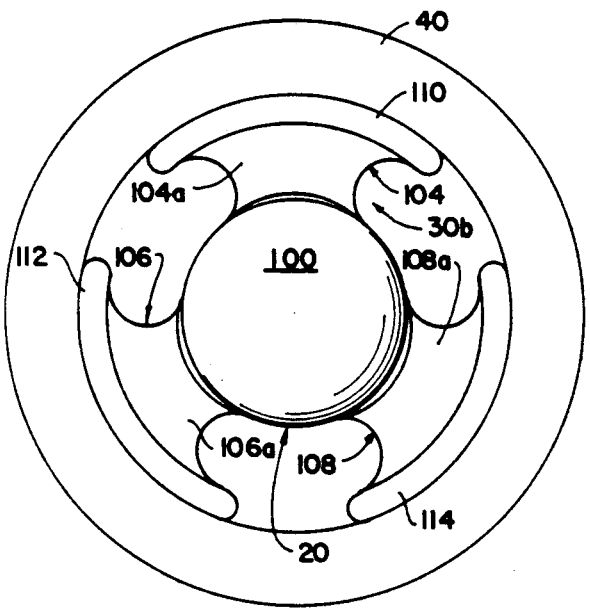
FIG. 3 is a front elevation view of the second embodiment of the present invention, including a schematic representation of the ciliary muscle in which the second embodiment is disposed.
Figure 4:
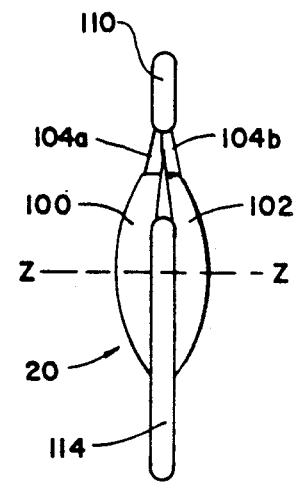
FIG. 4 is a side elevation view of the embodiment illustrated in FIG. 3.

Referring now to FIGS. 3 and 4, the lens assembly 20 of the second embodiment of the present invention comprises a pair of compound lenses 100 and 102 which are sized to fit within the sulcus of the ciliary muscle slightly in front of the capsule which encased the crystalline lens. Lenses 100 and 102 are preferably circular, have convex outer surfaces and have identical diameters and focal powers. Alternatively, the lenses may have different focal powers and may have plano-convex, fresnel or other outer surface configurations.

The haptics 30b of the second embodiment are designed to support lenses 100 and 102 in coaxial alignment and to transmit contraction and relaxation of the ciliary muscle 40 to the lenses 100 and 102 so as to cause the latter to move toward and away from one another along the center or Z (see FIG. 4) axes thereof, thereby changing the focal power of the lens assembly. In the most general sense, haptics 30b comprise two or more pairs of support members, which mechanically couple lenses 100 and 102 to the ciliary muscle 40. The support members are constructed to flex in a predetermined manner so as to transmit the contraction and relaxation motion of the ciliary muscle to the lenses, thereby causing the lenses to move toward and away from one another along their center axes. By selective positioning of the support members on the lenses and by proper definition of the points of flexure of the support members, haptics 30b will cause lenses 100 and 102 to move toward one another along the center axes thereof when the ciliary muscle relaxes and away from one another when the ciliary muscle contracts.

The haptics 30b of the second embodiment of the present invention may, for instance, comprise arm pairs 104, 106 and 108. Preferably, arm pairs 104, 106 and 108 are made from a plastic having suitable biological compatibility and selected flexure and strength characteristics. Each arm pair comprises two discrete portions which are secured together at one end thereof and are coupled to or integral with the lens 100 or 102 to which they are attached at the opposite ends thereof. More specifically, arm pair 104 comprises portions 104a (FIGS. 3 and 4) and 104b (FIG. 4) which are positioned adjacent to and are spaced slightly from one another. One end of portion 104a is attached to or is integral with lens 100, and one end of portion 104b is attached to or is integral with lens 102. The other ends of portions 104a and 104b are secured together, as described in greater detail hereinafter. Similarly, arm pair 106 comprises portions 106a (FIGS. 3) and 106b (not shown), each having one end which is attached to lenses 100 and 102, respectively, and having opposite ends which are attached together, as described in greater detail hereinafter. Arm pair 108 comprises portions 108a (FIG. 3) and 108b (not shown), each having one end which is attached to or is integral with lenses 100 and 102, respectively, and having opposite ends which are attached together, as described in greater detail hereinafter.

Arm pair portions 104a, 104b, 106a, 106b, 108a, and 108b are relatively stiff along their length, as measured along axes extending radially outwardly from lenses 100 and 102. Furthermore, the arm pair portions have defined points of flexure at their ends. Thus, the arm pair portions will flex at the ends thereof attached to lenses 100 and 102, as the case may be, will flex at the ends thereof which are attached together, and will tend not to flex along the length thereof. The arm pair portions are further biased, as described in greater detail hereinafter, so that when a radially inward force is applied to the ends of the arm pair portions which are attached together, the ends of the arm pair portions which are not attached together will spread apart from one another. These flexural characteristics are achieved, as is well known, by selective design of the arms and by proper choice of materials used to fabricate the arms.

Preferably, each of the arm pairs 104, 106 and 108 is secured to lenses 100 and 102 so as to be substantially equally spaced from adjacent arm pairs. Thus, each of the arm pairs is spaced about 120° from adjacent arm pairs.

Haptics 30b further comprise curved end sections 110, 112 and 114. The thickness and radius of curvature of the latter as well as the length of arm pairs 104, 106, and 108, are selected to permit the end sections to fit securely within the sulcus of the ciliary muscle 40, even when the latter is fully relaxed. The radially-outermost ends of arm pair portions 104a and 104b are secured together at or are integral with curved end section 110, the radially-outermost ends of arm pair portions 106a and 106b are secured together at or are integral with curved end section 112, and the radially-outermost ends of arm pair portions 108a and 108b are secured together at or are integral with curved end section 114.

The flexural bias of the arm pairs 104, 106, and 108 and the thickness of lenses 100 and 102 must, of course, be selected, given the space constraints of the capsule within which the accommodating intraocular lens is implanted, to permit the lenses to reach maximum spacing along the Z axis relative to one another.

The haptics 30b of the second embodiment illustrated in FIGS. 3 and 4 are only exemplary of the structure the haptics may take. It should be appreciated that the haptics of the second embodiment may comprise a wide range of structure, the only requirements being that the haptics (a) securely support lenses 100 and 102 within the eye and (b) translate the contraction and relaxation movement of the ciliary muscle into forces which move the lenses 100 and 102 toward and away from one another along their center axes.

Alternatively, the second embodiment may comprise more than two coaxially disposed lenses. In this case, the haptics are designed to move the lenses along the center axes thereof so that when the ciliary muscle contracts the focal power of the lens assembly increases and when the ciliary muscle relaxes the focal power of the lens assembly decreases. Of course, the haptics must be designed and the thickness of the lenses selected so that the lens assembly can move through its full range of travel within the space provided in the capsule or the sulcus of the ciliary muscle in which the accommodating intraocular lens is received.

Figure 5:
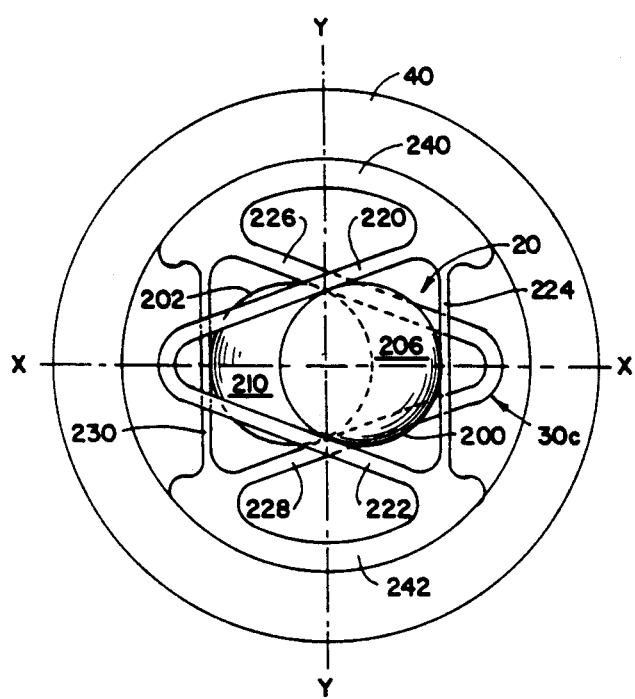
FIG. 5 is a front elevation view of a third embodiment of the present invention, including a schematic representation of the ciliary muscle in which the third embodiment is disposed.
Figure 6:
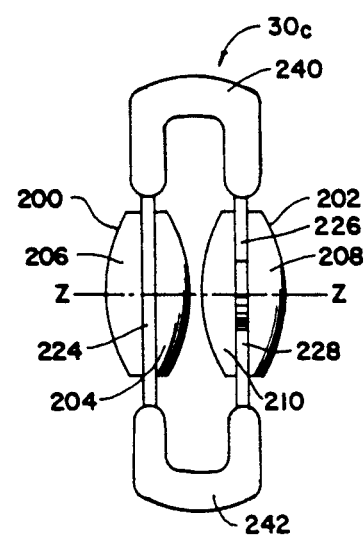
FIG. 6 is a side elevation view of the embodiment illustrated in FIG. 5.

Referring to FIGS. 5 and 6, the lens assembly 20 of the third embodiment of the present invention comprises progressive power lenses 200 and 202. The latter are substantially identical to progressive power lens 50. Thus, progressive power lens 200 has a convex base power surface 204 and a progressive power surface 206, and progressive power lens 202 has a convex base power surface 208 and a progressive power surface 210. As with progressive lens 50, base power surfaces 204 and 208 may also be progressive, planar or may take the configuration of a fresnel lens.

Lenses 200 and 202 preferably have an identical diameter and range and distribution as (measured along the X axis in FIG. 5) of focal powers. Lenses 200 and 202 are positioned so that progressive power surface 210 of lens 202 faces base power surface 204 of progressive power lens 200. Lenses 200 and 202 are also positioned so that the center or Z axes (see FIG. 6) axes thereof are coaxial or extend to parallel and lie on a plane extending perpendicular to the X and Y axes, as seen in FIG. 5. Lenses 200 and 202 are further positioned so that the higher power side of the lenses, i.e. the side of the lenses having the smallest radius of curvature, are disposed in diametric opposition.

The adjustment mechanism, or haptics, 30c of the third embodiment of the present invention is designed to support lenses 200 and 202 so as to achieve the above-described relative positioning of the lenses. Haptics 30c are further designed to transmit contraction and relaxation motion from the ciliary muscle 40 to lenses 200 and 202 so as to cause the lenses to move back and forth in opposite directions along the X axis, as viewed in FIG. 5, normally to the center or Z axis, as viewed in FIG. 6. In the most general sense haptics, 30c comprise four or more support members for mechanically coupling the lenses 200 and 202 with the ciliary muscle 40. Two of the support members engage lens 200 and the other two of the support members engage lens 202.

The support members are constructed to have specifically defined points of flexure. The portions of lenses 200 and 202 which are engaged by the support members and the flexure characteristics of the support members are chosen so that (a) when the ciliary muscle 40 contracts, lens 200 is driven to the left along the X axis and lens 202 is driven to the right along the X axis, as viewed in FIG. 5, and (b) when ciliary muscle 40 relaxes lens 200 is driven to the right along the X axis and lens 202 is driven to the left along the X axis, as viewed in FIG. 5.

Referring to FIGS. 5 and 6, the haptics 30c of the third embodiment of the present invention may, for instance, comprise elongate arms 220, 222 and 224 and elongate arms 226, 228 and 230. Both of these groups of arms are substantially identical to arms 60, 62 and 64 of the exemplary first embodiment of present invention. Thus, arms 220-230 are made from a plastic having suitable biological compatibility and selected flexure and strength characteristics. A central portion of each of the arms 220, 222 and 224 engages, is secured to or is integral with the outer edge of lens 200, with the arms being positioned so that the central portion of each arm is separated by about 120° from the central portions of adjacent arms, as measured around the circumference of lens 200. Similarly, a central portion of each of the arms 226, 228 and 230 engages, is attached to, or is integral with the outer edge of lens 202, with the arms being positioned so that the central portion of each arm is separated by about 120° from the central portions of adjacent arms, as measured around the circumference of lens 202.

More specifically, arm 224 is attached to the circumferential edge of lens 200 at the 3 o'clock position, as viewed in FIG. 5, and arm 230 is attached to the circumferential edge of lens 202 at the 9 o'clock position, as viewed in FIG. 5. Thus, arm 224 is attached to the edge of the highest power portion of lens 200 and arm 230 is attached to the edge of the highest power portion of lens 202. By this positioning, arms 224 and 230 extend substantially in parallel with one another and with the Y axis. Arms 220 and 222 slidingly engage the circumferential edge of lens 200 and arms 226 and 228 slidingly engage the circumferential edge of lens 202. Alternatively, lens 200 may be positioned so that its low power side is attached to arm 224, and lens 202 may be positioned so that its low power side is attached to arm 230. Optionally, an upstanding flange may be provided extending along the length of the inner edge of arms 220, 222, 226, and 228 and a groove may be provided in the circumferential edges of lens 200 sized to receive the flanges on arms 220 and 222 with a sliding fit and a groove may be provided in the circumferential edge of lens 202 sized to receive the flanges on arms 226 and 228 with a sliding fit. Alternatively, a groove (not shown) may be provided along the length of the inner edge of arms 220, 222, 226 and 228 and a flange (not shown) may be provided on the circumferential edges of lens 200 sized to be received in the grooves in arms 220 and 222 with a sliding fit and a flange (not shown) may be provided in the circumferential edges of lens 202 sized to be received in the grooves in arms 226 and 228 with a sliding fit.

Arms 220 and 222 are more resistant to flex along their length than arm 224. Similarly, arms 226 and 228 are more resistant to flex along their length than arm 230. Preferably, arm 224 is biased to flex inwardly to the left, as seen in FIG. 5, when a compressive force is applied to the ends of arm 224. Preferably, arm 230 is biased to flex inwardly to the right, as seen in FIG. 5, when a compressive force is applied to the ends of arm 230. Alternatively, arm 224 may be biased to flex outwardly to the right and arm 230 may be biased to flex outwardly to the left when compressive forces are applied to the ends of the arms. These flexural characteristics are achieved, as one of ordinary skill in the art will readily appreciate, by selective design of the arms and by proper choice of the materials used to fabricate the arms.

The haptics 30c of the third embodiment further comprise curved bridges 240 and 242. The thickness and radius of curvature of bridges 240 and 242, as well as the length of arms 220-230, are selected to permit the former to fit securely within the sulcus of the ciliary muscle 40 even when the latter is fully relaxed.

The ends of arms 220 and 224 are secured to or are integral with bridge 240, the ends of arms 220 and 222 are secured together at a location that is radially inward of bridges 240 and 242, and the ends of arms 222 and 224 are secured to or are integral with bridge 242. The ends of arms 226 and 230 are secured to or are integral with bridge 240, the ends of arms 226 and 228 are secured together at a location that is radially inward of bridges 240 and 242, and arms 228 and 230 are secured to or are integral with bridge 242.

The lengths of arms 220, 222 and 224 are selected so that each of the curved bridges 240 and 242 are separated by about 180° from one another. Preferably, arms 220 and 222 are secured to bridges 240 and 242 so as to lie along a first plane and arm 224 is secured to bridges 240 and 242 so as to lie along a second plane that is spaced from but extends in parallel with the first plane. Preferably, arms 226 and 228 are secured to bridges 240 and 242 so as to lie along a third plane and arm 230 is secured to bridges 240 and 242 so as to lie along a fourth plane that is spaced from but extends in parallel with the third plane. The first and second planes are spaced from and extend in parallel with the third and fourth planes.

Arms 220-230 and bridges 240 and 242 are further sized and arranged so that when ciliary muscle 40 is completely relaxed, about the left third of lens 200 will overlap about the right third of lens 202. Similarly, when the ciliary muscle is fully contracted, about the right third of lens 200 will overlap about the left third of lens 202.

The haptics 30c of the third embodiment, as illustrated in FIGS. 5 and 6, are only exemplary of the structure the haptics may take. Thus, it should be appreciated that the haptics of the third embodiment may comprise a wide range of structure, the only requirements being that the haptics (a) securely support lenses 200 and 202 within the eye, (b) translate contraction of the ciliary muscle 40 so as to cause lens 200 to move to the left along the X axis and lens 202 to move to the right along the X axis, normally to the Z axis and (c) translate relaxation of the ciliary muscle so as to cause lens 200 to move to the right along the X axis and lens 202 to move to the left along the X axis, normally to the Z axis.

Operation

In the following description of the operation of the three embodiments of the present invention reference will be made to the exemplary versions of the embodiments described above and illustrated in FIGS. 1-6. As will be apparent to those of ordinary skill in the art, other versions of the three embodiments embraced by the present invention and not specifically illustrated or described above function in accordance with the operating principles set out hereinafter.

Referring first to FIGS. 1 and 2, the accommodating intraocular lens of the first embodiment of the present invention is implanted into an eye using conventional techniques for implanting known intraocular lenses. During the implantation procedure, curved end portions 70, 72 and 74 are inserted into the sulcus of the ciliary muscle. As note above, curved end portions 70, 72 and 74 and arms 60, 62, and 64 are sized so that the end portions will remain disposed in the sulcus even when the ciliary muscle is completely relaxed.

When ciliary muscle 40 is completely relaxed, haptics 30a assume the position illustrated in FIG. 1. In this position, arms 60, 62, and 64 are substantially straight and lens 50 is positioned so that its low power side, i.e., the left side as shown in FIG. 1, is substantially centered, as measured along the X axis, within the aperture of the ciliary muscle. In this position, the low power side of lens 50 is on the center axis of the eye. As a result of this positioning, light rays reflected off distant objects that pass through the low power side of progressive lens 50 will appear in focus. The mind is able to substantially ignore the differently-focused light rays which pass through the intermediate or high power side of lens 50 and reach the retina, with the result that the distant objects appear in focus.

When ciliary muscle 40 begins to contract, curved end portions 70, 72, and 74 are forced radially inwardly. Because arm 62 is biased to flex inwardly and because arm 62 is more resilient and hence yielding than arms 60 and 64, the radially inward force applied to curved portions 70, 72 and 74 causes the center of arm 62 to flex inwardly to the left along the X axis as seen in FIG. 1. The central axis of ciliary muscle 40 extends perpendicular to the X and Y axes, and coaxially with the Z axis, as seen in FIGS. 1 and 2. Arm 62 may be positioned to extend along a different plane than arms 60 and 64, as discussed above, to facilitate this flexure.

Because arm 62 is attached to lens 50 at the 3 o'clock position, as arm 62 flexes inwardly, it pushes lens 50 inwardly to the left as seen in FIG. 1. Because arms 60 and 64 merely engage the circumferential edge of lens 50, as arm 62 pushes lens 50 to the left the latter slides along the inner edge of arms 60 and 64. As a result of their resilient nature, arms 60 and 64 tend to bow outward somewhat as lens 50 is pushed to the left along the X axis by arm 62. Thus, the radially inward force provided by ciliary muscle 40 is translated by haptics 30a into a linear force which causes lens 50 to move to the left along the X axis.

Upstanding flanges (not shown) may be provided extending along the inner edges of arms 60 and 64, and a groove sized to accommodate the flanges with a sliding fit may be provided on the circumferential edge of lens 50, as noted above, to ensure lens 50 remains engaged with arms 60 and 64 during the above-described sliding motion of the lens along the arms.

As indicated above, the light rays which pass through that portion of lens 50 at the center of the aperture of ciliary muscle 40, as measured along the X axis, appear in focus. Other light rays passing through portions of progressive lens 50 which are not centered in the aperture of ciliary muscle 40 and which reach the retina of the eye will be out of focus. However, the mind is able to substantially ignore these other rays.

When the person in whose eye the accommodating intraocular lens of the first embodiment is implanted changes his or her view from a distant to a close or intermediately-positioned object, the latter object will momentarily appear out of focus because the light rays reaching the retina will have passed through the lower power side of the lens. The person's mind recognizes this condition and applies appropriate stimuli to the ciliary muscle causing the latter to contract. As discussed above, this contraction causes arm 62 to flex inwardly so as to cause progressive power lens 50 to move to the left along the X axis. The mind will cause the ciliary muscle 40 to contract and thereby move lens 50 to the left as seen in FIG. 1 until that portion of progressive power surface 54 having the "proper" radius of curvature is positioned in the center of the aperture of the ciliary muscle. In this context, the proper radius of curvature is that radius which refracts the light rays reflected off the close or intermediately-positioned object being viewed such that the object appears in focus.

Thus, a closed-loop, constant feedback system exists between the mind and the ciliary muscle.. As the person in whom the intraocular lens of the first embodiment is implanted changes his or her view from an object positioned at a first distance to an object(s) positioned at a second distance, the mind will cause the ciliary muscle to contract or relax as needed so as to cause progressive lens 50 to move to the left and right, respectively, along the X axis as seen in FIG. 1. This movement continues until the portion of the lens which refracts the incoming light rays such that the object(s) being viewed appears in focus is centered along the X axis within the aperture of the ciliary muscle.

As discussed above, arm 62 may be provided with an outward bias and the progressive power lens 50 may be positioned so that the high focal power side is on the left of surface 54 and the low focal power side is on the right of surface 54. With this reversal of flexure and lens placement an accommodation capability can be achieved which is similar to that achieved with the exemplary version of the first embodiment discussed above. Thus, when a person focuses on a distant object the ciliary muscle relaxes and the low power side of progressive power lens 50 is centered in the aperture of the ciliary muscle. When the person views a close or intermediately-positioned object, the ciliary muscle in response to input stimuli from the mind contracts so as to cause arm 62 to flex outwardly and thereby draw higher focal power portions of progressive power lens 50 into the center of the aperture of ciliary muscle 40 until the object appears in focus.

Referring now to FIGS. 3 and 4, the accommodating intraocular lens of the second embodiment of the present invention is implanted into an eye in substantially the same manner as the accommodating intraocular lens of the first embodiment. Thus, curved end sections 110, 112 and 114 are inserted into the sulcus of ciliary muscle 40. Curved end sections 110, 112 and 114 and arm pairs 104, 106 and 108 are sized so that the end sections will remain disposed in the sulcus even when ciliary muscle is completely relaxed.

When ciliary muscle 40 is completely relaxed, haptics 30b assume the position illustrated in FIG. 4. In this position, the two portions of each of the arm pairs 104, 106 and 108, under the bias designed into the latter, contact or nearly contact one another. By virtue of the attachment of lenses 100 and 102 to the arm pair portions, when the latter are drawn together lenses 100 and 102 also contact or nearly contact one another. Thus, when the ciliary muscle is in the relaxed position, lenses 100 and 102 are urged toward one another along their center or Z axis under the bias of haptics 30b. In this position the overall thickness and hence focal power of the lens assembly is at a minimum. Thus, the lens assembly is positioned to permit the user thereof to focus clearly on distant objects.

When ciliary muscle 40 begins to contract, curved end sections 110, 112 and 114 are forced radially inwardly. Because both of the portions of each arm pair 104, 106 and 108 (a) are attached together only at the radially outermost ends thereof, (b) are outwardly biased, as measured along the Z axis in FIG. 4, and (c) are attached to curved end sections 110, 112 and 114, respectively, application of a radially inward force to the latter causes the radially innermost ends of the arm pair portions to spread apart along the Z axis.

As noted above, the arm pair portions are relatively stiff along their length and are provided with defined points of flexure at their opposite ends. As such, the above-described spreading of the inner ends of the arm pair portions is achieved by (a) the flexing of the radially-outermost ends of the arm pair portions relative to the curved end sections to which they are attached and (b) the flexing of the radially-innermost ends of the arm pair portions relative to lens 100 or 102 to which they are attached, as the case may be. Arm pairs 104, 106 and 108 are constructed in this manner to ensure the majority force applied radially inwardly to curved end sections 110, 112 and 114 is translated into spreading forces extending parallel to the Z axis.

As noted above, the radially-innermost ends of arm pair portions 104a, 106a, and 108a are attached to the circumferential edge of lens 100 and the radially-innermost ends of arm pair portions 104b, 106b 102. Because of this attachment, when muscle 40 contracts spreading the radially innermost ends of the arm pair portions away from one another along the Z axis, lenses 100 and 102 are urged away from one another along their center or Z axis. As the spacing between lenses 100 and 102, as measured along the Z axis, increases, the overall thickness and hence focal power of the lens assembly increases in continuous fashion.

When a person in whose eye the accommodating intraocular lens of the second embodiment is implanted changes his or her view from a distant object to a close or intermediately-positioned object, the latter will momentarily appear out of focus. In response, to this condition, the person's mind generates stimuli which cause the ciliary muscle to contract. As described above, this contraction causes the haptics 30b to flex so as to spread lenses 100 and 102 apart and thereby increase, in analog fashion, the focal power of the lens assembly. When lenses 100 and 102 are properly spaced, the latter will refract the incoming light rays such that the close or intermediately-positioned object appears in focus. In response to this condition, the mind will stop supplying the contraction stimuli to the ciliary muscle. As a result, the ciliary muscle will remain in a partially or totally contracted state, as the case may be depending upon the focal power required, and resultantly the object being viewed will remain in focus.

As with the first embodiment, a closed loop, constant feedback system exist between the mind and the ciliary muscle which produces accommodation in the intraocular lens of the second embodiment such that close, intermediately-positioned and distant objects can all be viewed in clear focus.

Referring now to FIGS. 5 and 6, the accommodating intraocular lens of the third embodiment of the present invention is implanted into an eye using the same techniques employed for implanting the lenses of the first and second embodiments, as described above. During the implantation procedure, curved bridges 240 and 242 are inserted into the sulcus of the ciliary muscle. As noted
above, curved bridges 240 and 242 and arms 220-230 are sized so that the bridges will remain disposed in the sulcus even when the ciliary muscle is completely relaxed.

When ciliary muscle 40 is completely relaxed, haptics 30c assume the position illustrated in FIG. 5. In this position, (a) arms 220-230 are substantially straight, (b) lens 200 is positioned so that its low power side, i.e. the left side as viewed in FIG. 5, is substantially centered, as measured along the X axis, within the aperture of the ciliary muscle, and (c) lens 202 is positioned so that its low power side, i.e. the right side as viewed in FIG. 5, is substantially centered, as measured along the X axis, within the aperture of the ciliary muscle. Thus, in the position illustrated in FIG. 5, approximately the left third of lens 200 overlaps approximately the right third of lens 202.

As a result of this positioning, light rays reflected off distant objects that pass through the low power side of progressive lenses 200 and 202, and hence through the center of the aperture of the ciliary muscle, will appear in focus. The mind is able to substantially ignore the differently-focused light rays which pass through the intermediate or high power sides of lenses 200 and 202 and reach the retina, with the result that the distant objects appear in focus.

When ciliary muscle 40 begins to contract, curved bridges 240 and 242 are forced radially inwardly. Because arm 224 is biased to flex inwardly to the left as seen in FIG. 5, and because arm 224 is more resilient and hence yielding than arms 220 and 222, when a compressive force is applied to arm 224 the center of arm 224 flexes inwardly to the left along the X axis as seen in FIG. 5.

Because arm 224 is attached to lens 200 at the 3o'-clock position, as arm 224 flexes inwardly, it pushes lens 200 inwardly to the left as seen in FIG. 5. Because arms 220 and 222 merely engage the circumferential edge of lens 200, as arm 224 pushes lens 200 to the left the latter slides along the inner edge of arms 220 and 222. Thus, the radially inward force provided by ciliary muscle 40 is translated by haptics 30c into a linear force which causes lens 200 to move to the left along the X axis.

Similarly, when ciliary muscle 40 begins to contract, curved bridges 240 and 242 apply a compressive force to arm 230. Because arm 230 is biased to flex inwardly to the right as seen in FIG. 5, and because arm 230 is more resilient and hence yielding than arms 226 and 228, the radially inward force applied to curved bridges 240 and 242 causes the center of arm 230 to flex inwardly to the right along the X axis as seen in FIG. 5.

Because arm 230 is attached to lens 202 at the 9o'-clock position, as arm 230 flexes inwardly, it pushes lens 202 inwardly to the right as seen in FIG. 5. Because arms 226 and 228 merely engage the circumferential edge of lens 202, as arm 230 pushes lens 202 to the right the latter slides along the inner edge of arms 226 and 228. Thus, the radially inward force provided by ciliary muscle 40 is translated by haptics 30c into a linear force which causes lens 202 to move to the right along the X axis.

Upstanding flanges (not shown) may be provided extending along the inner edges of arms 220 and 222, and a groove sized to accommodate the flanges with a sliding fit may be provided on the circumferential edge of lens 200, as noted above, to ensure lens 200 remains engaged with arms 220 and 222 during the above-described sliding motion of the lens along the arms. Similarly, upstanding flanges (not shown) may be provided extending along the inner edges of arms 226 and 228, and a groove sized to accommodate the flanges with a sliding fit may be provided on the circumferential edge of lens 202, as noted above, to ensure lens 202 remains engaged with arms 226 and 228 during the above-described sliding motion of the lens along the arms.

As discussed above, when the ciliary muscle is relaxed, light rays reflected off distant objects which pass through the low power sides of lens 200 and 202 (which are positioned at the center of the aperture of ciliary muscle 40, as measured along the X axis) appear in focus. Other light rays passing through portions of progressive lenses 200 and 202 which are not centered in the aperture of ciliary muscle 40 and which reach the retina of the eye will be out of focus. However, the mind is able to substantially ignore these other rays.

When the person in whose eye the third embodiment of the present accommodating intraocular lens is implanted changes his or her view from a distant to a close or intermediately-positioned object, the latter object will momentarily appear out of focus because the light rays reaching the retina will have passed through the lower power side of the lens. The person's mind recognizes this condition and applies appropriate stimuli to the ciliary muscle causing the latter to contract. As discussed above, this contraction causes arm 224 to flex inwardly to the left as seen in FIG. 5 so as to cause progressive power lens 200 to move to the left along the X axis. Similarly, inward contraction of the ciliary muscle causes arm 230 to flex inwardly to the right as seen in FIG. 5 so as to cause progressive power lens 202 to move to the right along the X axis.

The mind will cause the ciliary muscle 40 to contract and thereby move lens 200 to the left as seen in FIG. 5 and lens 202 to the right as seen in FIG. 5 until those portions of progressive power surfaces 206 and 210 having the "proper" radii of curvature are positioned in the center of the aperture of the ciliary muscle. In this context, the portions having the "proper" radii of curvature are those portions which refract the light rays reflected off the close or intermediately-positioned object being viewed such that the object appears in focus.

Thus, as with the other embodiments of the present invention, a closed-loop, constant feedback system exists between the mind and the ciliary muscle. As the person in whom the intraocular lens of the third embodiment is implanted changes his or her view from an object positioned at a first distance to an object(s) positioned at a second distance, the mind will cause the ciliary muscle to contract or relax as needed so as to cause progressive lenses 200 and 202 to move to the left and right along the X axis as seen in FIG. 5. This movement continues until those portions of the lenses which refract the incoming light rays such that the object(s) being viewed appears in focus are centered along the X axis within the aperture of the ciliary muscle.

As discussed above, arms 200 and 202 may be provided with an outward bias, progressive power lens 200 may be positioned so that its high focal power side is on the left of surface 206, and progressive power lens 202 may be positioned so that its high focal power side is on the right of surface 210. With this reversal of flexure and lens placement an accommodation capability is achieved which is similar to that achieved with the exemplary version of the third embodiment discussed above. Thus, when a person focuses on a distant object the ciliary muscle relaxes and the low power sides of progressive power lens 200 and 202 are centered in the aperture of the ciliary muscle. When the person views a close or intermediately-positioned object, the ciliary muscle in response to input stimuli from the mind contracts so as to cause (a) arm 224 to flex outwardly to the right as seen in FIG. 5 and (b) arm 230 to flex outwardly to the left as seen in FIG. 5. This flexure draws the higher focal power portions of progressive power lenses 100 and 102 into the center of the aperture of ciliary muscle 40 until the object appears in focus.

It is to be appreciated that with the first embodiment shown in FIGS. 1 and 2, lens 50 could be formed so that a progressive power surface is formed on both surface 52 and 54, with the higher power of one surface being coaxial along the viewing axis with the higher power of the other surface. A similar construction could be applied to each of the lenses 200 and 202 of the third embodiment of FIGS. 5 and 6.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. An adjustable-power intraocular lens comprising:
   lens means adapted for implantation in an eye, for causing light rays entering the eye to converge at a selected focal point or plane, the location of which varies along a first axis in analog fashion between first and second locations with movement of said lens means along a selected axis between first and second positions on said selected axis wherein said selected axis extends substantially perpendicular to said first axis; and
   adjustment means connected to said lens means and couplable to the ciliary muscle of said eye for causing said lens means to move along said selected axis between said first and second positions in response to contraction and relaxation of said ciliary muscle.

2. An adjustable-power intraocular lens according to claim 1 wherein said lens means comprises a progressive power lens.

3. An adjustable-power intraocular lens according to claim 2 wherein said progressive power lens comprises a progressive power surface and a base power surface, said progressive power surface having a plurality of different radii of curvature arranged so that the radii of curvature increase continuously from a first side of said progressive power surface to a second diametrically opposed side of said progressive power surface.

4. An adjustable-power intraocular lens according to claim 1 wherein said adjustment means causes said lens means to move (1) toward said first position when said ciliary muscle relaxes and (2) toward said second position when said ciliary muscle contracts.

5. An adjustable-power intraocular lens according to claim 3, said adjustment means comprising at least two flexible support members coupled to selected portions of said progressive power lens and couplable to said ciliary muscle, each of said at least two support members having selectively defined points of flexure, said selected portions of said progressive power lens and said selectively defined flexure points of said at least two support arms being chosen so that (a) when said ciliary muscle contracts said at least two support members flex so as to cause said progressive power lens to move along said selected axis away from said first position and toward said second position and (b) when said ciliary muscle relaxes said at least two support members flex so as to cause said progressive power lens to move along said selected axis away from said second position and toward said first position.

6. An adjustable-power intraocular lens according to claim 5, wherein said second side of said progressive power surface is substantially centered in the aperture of said ciliary muscle, as measured along said selected axis, when said progressive power lens is in said first position and said first side of said progressive power surface is substantially centered in the aperture of said ciliary muscle when said progressive power lens is in said second position.

7. An adjustable-power intraocular lens according to claim 5 wherein said at least two flexible support members comprise three elongate arms secured together so as to define a triangularly-shaped structure, one of said elongate arms being more flexible along its length than the other two elongate arms.

8. An adjustable-power intraocular lens according to claim 7, wherein said one elongate arm is flexurally biased so that when a compressive force is applied to the ends of said one elongate arm a mid-length portion thereof will flex in the direction said progressive power lens moves when the latter is caused to move along said selected axis from said first position to said second position.

9. An adjustable-power intraocular lens according to claim 1, wherein said lens means comprises first and second progressive power lenses positioned adjacent one another so that the center axes thereof (1) extend substantially in parallel, and (2) lie substantially along a plane which lies along said selected axis.

10. An adjustable-power intraocular lens according to claim 9, wherein said first and second progressive power lenses each have a progressive power surface and a base power surface, said progressive power surfaces each having a plurality of different radii of curvature arranged so that the radii of curvature increase continuously from a first side to a second side of said progressive power surfaces.

11. An adjustable-power intraocular lens according to claim 10, wherein said first and second progressive power lenses are positioned so that said first side of said first progressive lens is diametrically opposed to said first side of said second progressive lens.

12. An adjustable-power intraocular lens according to claim 9 further wherein:
   (a) when said lens assembly is in said first position, said first progressive power lens is in a first position and said second progressive power lens is in a second position; and
   (b) when said lens assembly is in said second position, said first progressive power lens is in a second position and said second progressive power lens is in a first position.

13. An adjustable-power intraocular lens according to claim 12, wherein said adjustment means comprises:
   (a) at least two flexible support members coupled to selected portions of said first progressive power lens and couplable to said ciliary muscle, each of said at least two support members having selectively defined points of flexure, said selected portions of said first progressive power lens and said selectively defined flexure points of said at least two support arms being chosen so that (a) when said ciliary muscle contracts said at least two support members flex so as to cause said progressive power lens to move along said selected axis away from said first position and toward said second position and (b) when said ciliary muscle relaxes said at least two support members flex so as to cause said progressive power lens to move along said selected axis away from said second position and toward said first position; and (b) at least two flexible support members coupled to selected portions of said second progressive power lens and couplable to said ciliary muscle, each of said at least two support members having selectively defined points of flexure, said selected portions of said second progressive power lens and said selectively defined points of flexure of said at least two support arms being chosen so that (a) when said ciliary muscle contracts said at least two support members flex so as to cause said second progressive power lens to move along said selected axis away from said second position and toward said first position and (b) when said ciliary muscle relaxes said at least two support members flex so as to cause said second progressive power lens to move along said selected axis away from said first position and toward said second position.

14. An accommodating intraocular lens comprising: at least one lens, the power of which is adjustable by moving said at least one lens along an axis between first and second focal positions, said at least one lens being designed for implantation in an eye having a ciliary muscle which is capable of expanding and contracting radially about a central axis; and a haptic assembly, couplable to said at least one lens and adapted to transmit movement from the ciliary muscle of said eye to said at least one lens to that said at least one lens moves along said axis between said first and second focal positions in response to contraction and relaxation of said ciliary muscle, wherein said axis extends substantially perpendicular to said central axis of said ciliary muscle.

15. An adjustable-power intraocular lens comprising:
a first lens which is adapted for implantation in an eye;
a second lens which is adapted for implantation in said eye proximate said first lens; and
adjustment means connected to said first and second lenses and couplable to the ciliary muscle of the eye (1) for supporting said first and second lenses adjacent one another so that the center axes thereof are substantially coaxial, and (2) for causing said first and second lenses to move (a) apart from one another along said center axes thereof in response to contraction of said ciliary muscle and (b) toward one another along said center axes thereof in response to relaxation of said ciliary muscle.

16. An adjustable-power intraocular lens according to claim 15 wherein said adjustment means comprises a plurality of flexible support members coupled to selected portions of said first and second lenses and couplable to said ciliary muscle, each of said plurality of support members having selectively defined points of flexure, said selected portions of said first and second lenses and said selectively defined points of flexure of said plurality of support members being chosen so that (a) when said ciliary muscle contracts said plurality of support members flex so as to cause said first and second lenses to move along said central axes thereof away from one another and (b) when said ciliary muscle relaxes said plurality of support members flex so as to cause said first and second lenses to move along said central axes thereof toward one another.

17. An adjustable-power intraocular lens according to claim 15 wherein said first and second lenses have a convex outer surface.

* * * * *